(12) United States Patent
Miller et al.

(10) Patent No.: US 11,742,068 B2
(45) Date of Patent: Aug. 29, 2023

(54) USER SIGNALING THROUGH A PERSONAL CARE DEVICE

(71) Applicant: L'Oreal, Paris (FR)

(72) Inventors: Zane Bowman Allen Miller, Seattle, WA (US); Jeffrey Kissinger, Kirkland, WA (US); Geoffrey F. Deane, Bellevue, WA (US)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 17/463,023

(22) Filed: Aug. 31, 2021

(65) Prior Publication Data

US 2021/0398644 A1 Dec. 23, 2021

Related U.S. Application Data

(62) Division of application No. 16/452,299, filed on Jun. 25, 2019, now abandoned.

(51) Int. Cl.

| | |
|---|---|
| *G16H 20/40* | (2018.01) |
| *G16H 40/63* | (2018.01) |
| *G08B 7/06* | (2006.01) |
| *G08B 21/18* | (2006.01) |
| *G08B 25/00* | (2006.01) |

(52) U.S. Cl.
CPC ............ *G16H 20/40* (2018.01); *G08B 7/06* (2013.01); *G08B 21/18* (2013.01); *G08B 25/001* (2013.01); *G16H 40/63* (2018.01)

(58) Field of Classification Search
CPC .......... G16H 20/40; G16H 40/63; G08B 7/06; G08B 21/18; G08B 25/001; A46B 15/0006; A46B 15/004; A46B 13/008; A46B 2200/102; G06F 16/95
See application file for complete search history.

(56) References Cited

U.S. PATENT DOCUMENTS

| | | | |
|---|---|---|---|
| 8,923,804 B1 | 12/2014 | Aldridge, II et al. | |
| 9,301,598 B2 | 4/2016 | Hyde et al. | |
| 9,757,065 B1 * | 9/2017 | Suri | A61B 1/247 |

(Continued)

FOREIGN PATENT DOCUMENTS

| | | | |
|---|---|---|---|
| KR | 2020-0027317 A | 3/2020 | |
| WO | WO-2018065374 A1 * | 4/2018 | A46B 11/0006 |

OTHER PUBLICATIONS

International Search Report and Written Opinion dated Sep. 11, 2020, issued in corresponding International Application No. PCT/US2020/039422, filed Jun. 24, 2020, 13 pages.

*Primary Examiner* — Adnan Aziz
(74) *Attorney, Agent, or Firm* — CHRISTENSEN O'CONNOR JOHNSON KINDNESS PLLC

(57) ABSTRACT

A personal care device that is capable of two-way communication is provided. In some embodiments, the personal care device operates in a first mode and a second mode depending on whether a signal has been received from a networked computing device, thus allowing a single human-machine interface (HMI) device to both control the personal care device and to cause signals to be sent to the networked computing device. In some embodiments, the personal care device is configured to present media streamed from the networked computing device, and/or to stream audio detected by the personal care device to the networked computing device.

17 Claims, 6 Drawing Sheets

(56) References Cited

U.S. PATENT DOCUMENTS

| | | |
|---|---|---|
| 10,664,074 B2 | 5/2020 | Moussette et al. |
| 10,739,974 B2 | 8/2020 | Wilson et al. |
| 2002/0115478 A1 | 8/2002 | Fujisawa et al. |
| 2004/0066710 A1 | 4/2004 | Yuen et al. |
| 2004/0249672 A1* | 12/2004 | Bocionek ............... G16H 50/20 705/2 |
| 2007/0179413 A1 | 8/2007 | Imboden et al. |
| 2008/0180306 A1* | 7/2008 | McRae ................. G08C 23/04 341/176 |
| 2009/0064430 A1* | 3/2009 | Jimenez ............. A46B 15/0008 15/22.1 |
| 2010/0281636 A1* | 11/2010 | Ortins ...................... A46B 9/04 15/4 |
| 2011/0009725 A1* | 1/2011 | Hill ........................ A61B 5/157 705/28 |
| 2013/0040610 A1 | 2/2013 | Migicovsky et al. |
| 2013/0081479 A1 | 4/2013 | Miller et al. |
| 2014/0320284 A1 | 10/2014 | Messenger et al. |
| 2015/0122018 A1 | 5/2015 | Yuen |
| 2015/0230863 A1* | 8/2015 | Youngquist .......... A61B 18/203 606/9 |
| 2015/0230899 A1* | 8/2015 | Vetter ................ A46B 15/0004 15/22.1 |
| 2015/0294639 A1* | 10/2015 | McCoy .................. G09B 21/00 345/173 |
| 2015/0342515 A1 | 12/2015 | Hutchings et al. |
| 2016/0338807 A1 | 11/2016 | Bloch et al. |
| 2017/0056146 A1 | 3/2017 | Boughorbel |
| 2017/0084189 A1 | 3/2017 | Rubalcaba et al. |
| 2017/0116665 A1* | 4/2017 | Alzahrani ............ A46B 5/0025 |
| 2017/0172715 A1 | 6/2017 | Duong et al. |
| 2017/0345283 A1 | 11/2017 | Kwon et al. |
| 2017/0367543 A1* | 12/2017 | Straka .................... A61H 7/005 |
| 2017/0372634 A1 | 12/2017 | Straka et al. |
| 2018/0019929 A1 | 1/2018 | Chen et al. |
| 2018/0027940 A1* | 2/2018 | Goldman ............ H01M 50/213 |
| 2018/0033205 A1 | 2/2018 | Kong et al. |
| 2018/0085942 A1 | 3/2018 | Perez Lopez et al. |
| 2018/0092449 A1 | 4/2018 | Straka et al. |
| 2018/0120420 A1 | 5/2018 | McMahon et al. |
| 2018/0184796 A1 | 7/2018 | Balooch et al. |
| 2018/0196522 A1* | 7/2018 | Rochford ................ G06F 3/011 |
| 2018/0211509 A1 | 7/2018 | Ramaci |
| 2019/0075922 A1 | 3/2019 | Rivera et al. |
| 2019/0209078 A1 | 7/2019 | Charraud et al. |
| 2019/0251860 A1 | 8/2019 | Lawrenson et al. |
| 2019/0306259 A1 | 10/2019 | Burghardt et al. |
| 2020/0029680 A1* | 1/2020 | Farrell ..................... G08B 7/06 |
| 2020/0268141 A1* | 8/2020 | Newman ............. A46B 5/0095 |
| 2021/0056828 A1 | 2/2021 | Ten Kate et al. |

\* cited by examiner

USER SIGNALING THROUGH A PERSONAL CARE DEVICE

CROSS-REFERENCES TO RELATED APPLICATIONS

This application is a division of U.S. application Ser. No. 16/452,299, filed Jun. 25, 2019, the entire disclosure of which is hereby incorporated by reference herein for all purposes.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a method of controlling operation of a treatment application device of a personal care device is provided. The treatment application device is started in response to detecting a first actuation of an HMI device of the personal care device. While the treatment application device is running, a second actuation of the HMI device is detected. A determination is made regarding whether the personal care device is operating in a first mode or a second mode. In response to determining that the personal care device is operating in the first mode, the treatment application device is stopped. In response to determining that the personal care device is operating in the second mode, a signal is transmitted via a network interface of the personal care device to a networked computing device.

In some embodiments, a system is provided. The system comprises a personal care device and a networked computing device. The personal care device includes a treatment application device and a network interface. The networked computing device includes a network interface. The personal care device and the networked computing device are configured to communicate bidirectionally via the network interface of the personal care device and the network interface of the networked computing device.

In some embodiments, a personal care device is provided. The personal care device comprises a treatment application device, a human-machine interface (HMI) device, a network interface, circuitry for receiving signals from a networked computing device via the network interface, and circuitry for transmitting signals to the networked computing device via the network interface.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Personal care devices are increasingly helping people improve their daily routines, whether it is for skincare, dental care, or other personal care tasks. However, the recommended treatment cycles for personal care devices can sometimes take a longer amount of time than may be easy to fit within a normal morning or evening routine. While using the personal care device to apply a treatment, the user may have to interrupt the treatment cycle in order to, for example, stop an alarm or other alert being presented by their smartphone or other networked computing device, or to answer a call received by their smartphone. What is desired are personal care devices with additional functionality to allow remote operation of networked computing devices via the personal care device, in order to provide greater compliance with recommended treatment cycles, and to otherwise increase the functionality of the personal care devices in order to make the devices more likely to be used.

Figure 1:
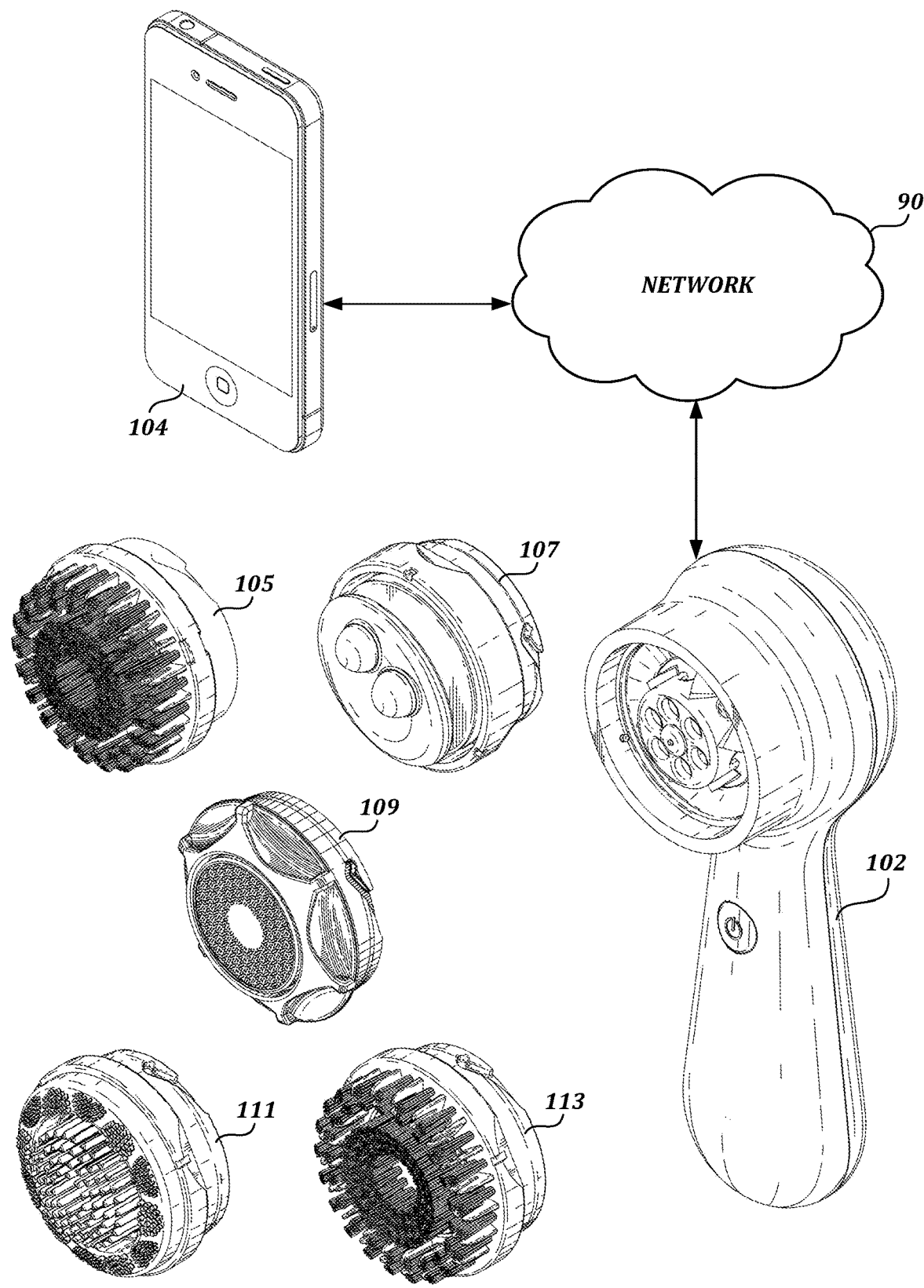
FIG. 1 is a schematic drawing that illustrates an example embodiment of a system that provides two-way communication with a personal care device according to various aspects of the present disclosure.

FIG. 1 is a schematic drawing that illustrates an example embodiment of a system that provides two-way communication with a personal care device according to various aspects of the present disclosure. The personal care device 102 may be coupled with a variety of attachments, including but not limited to the illustrated daily use cleaning brush head 105, an eye massaging head 107, a foundation makeup brush head 109, an exfoliating head 111, and a sensitive skin brush head 113. The personal care device 102 may be able to detect a type of attachment that is connected to it.

As shown, the personal care device 102 communicates with a networked computing device 104 (such as a smartphone) via a network 90. The network 90 may be any suitable type of network, including but not limited to a wireless network such as Bluetooth, Wi-Fi, 2G, 3G, 4G, LTE, or NFC; and a wired network such as Ethernet, USB, FireWire, or the Internet.

In some embodiments, bi-directional communication may be established between the networked computing device 104 and the personal care device 102. This allows for a variety of new functionalities to be provided. For example, in some embodiments, a human-machine interface (HMI) device of the personal care device 102 can be used to send inputs to the networked computing device 104. This can allow a user to cancel an alarm or other alert being presented by the networked computing device 104 without stopping the treatment cycle. In some embodiments, a single HMI device may be used to both control operation of the personal care device 102 and also to send signals to the networked computing device 104 depending on an operating mode of the personal care device 102, thus allowing the interface of the personal care device 102 to be simplified.

In some embodiments, the personal care device 102 may include a loudspeaker. In such embodiments, the personal care device 102 may receive information from the networked computing device 104 such as streaming media, and the personal care device 102 may present the streaming media via the loudspeaker 208 (or modulate the operation of a treatment application device 202 in coordination with the streaming media) in order to enhance the use experience. In some embodiments, the personal care device 102 may include both a loudspeaker and a microphone. In such embodiments, the personal care device 102 may be usable as a Bluetooth headset for responding to calls received by the networked computing device 104, for responding to voice calls in a messaging app received by the networked computing device 104, or for dictating responses to text-based messages received by the networked computing device 104. In some embodiments, the microphone of the personal care device 102 may also be used to monitor the environment around the personal care device 102, and the personal care device 102 may transmit monitored information to the networked computing device 104 for further processing. For example, the microphone may be used to monitor water use, and information about water use may be transmitted to the networked computing device 104. As another example, audio data captured by the microphone may be transmitted by the personal care device 102 for use as input by a smart speaker or other voice assistant, which may then take further action based on the audio data.

Figure 2:
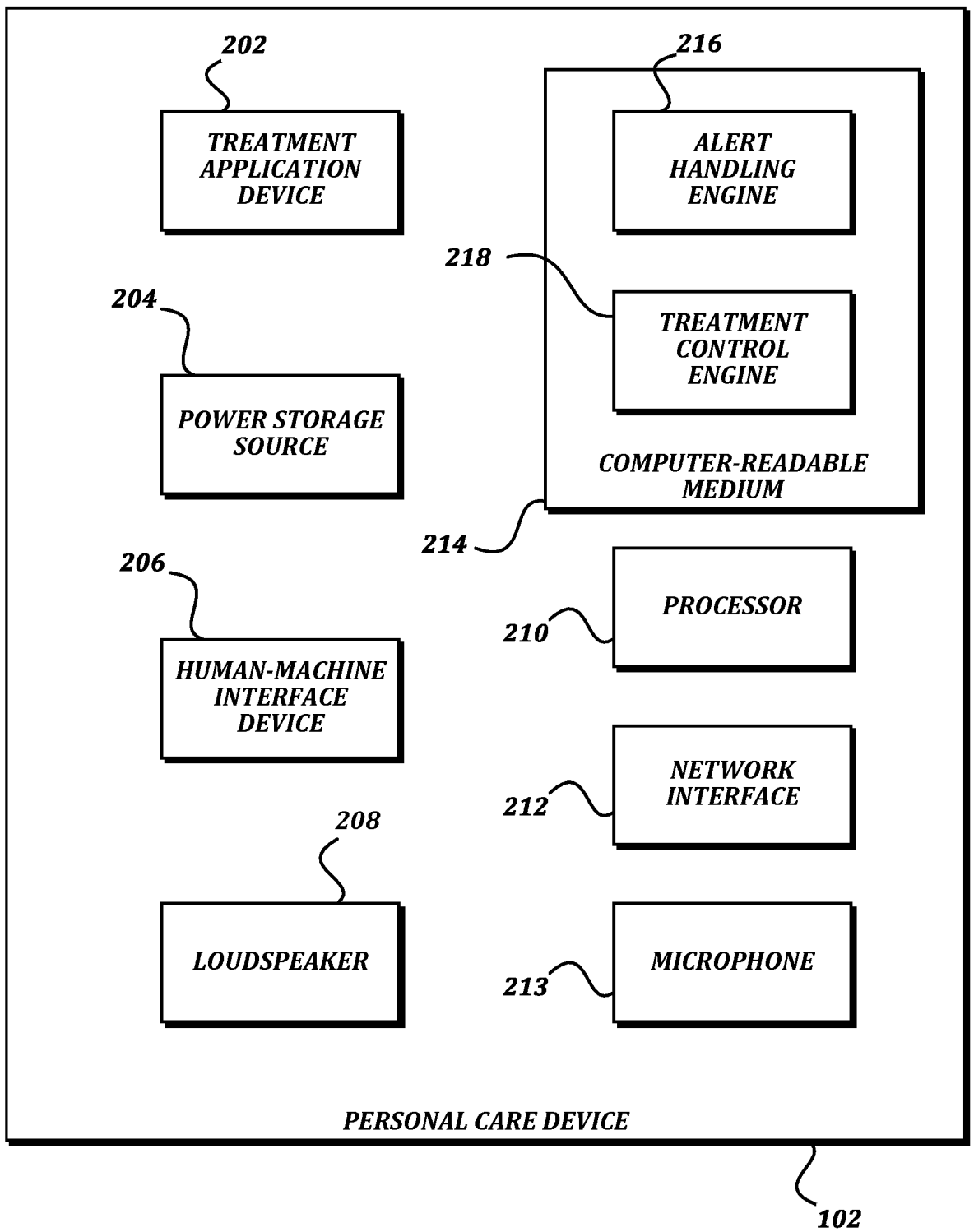
FIG. 2 is a block diagram that illustrates components included in an example embodiment of a personal care device according to various aspects of the present disclosure.

FIG. 2 is a block diagram that illustrates components included in an example embodiment of a personal care device according to various aspects of the present disclosure. In some embodiments, the personal care device 102 is any type of powered device that can be used as part of a daily personal care routine. One non-limiting example of a personal care device 102 is a powered brush with an interchangeable head that oscillates, rotates, or otherwise moves in order to perform a scrubbing action. Another non-limiting example of a personal care device 102 is a handheld light-emitting device that may be used to expose skin to light to achieve therapeutic benefits.

In the illustrated embodiment, the personal care device 102 includes a treatment application device 202, a power storage source 204, a human-machine interface device 206, a loudspeaker 208, a microphone 213, a processor 210, a network interface 212, and a computer-readable medium 214.

In some embodiments, the treatment application device 202 includes one or more devices that collectively apply a treatment to a user. For example, if the personal care device 102 is a powered brush, the treatment application device 202 may include a drive motor, an armature coupled to the drive motor that accepts a detachable brush head, and the brush head itself. As another example, if the personal care device 102 is a handheld light-emitting device, the treatment application device 202 may include one or more light-emitting diodes (LEDs), lasers, or other light-emitting devices.

In some embodiments, the power storage source 204 is a device, such as a rechargeable battery, that provides power to the treatment application device 202 for operation. In some embodiments, the power storage source 204 may also provide power for operation to the other components of the personal care device 102. In some embodiments, instead of a power storage source 204, the personal care device 102 may be coupled to an external power source, such as a wall power outlet.

In some embodiments, the human-machine interface (HMI) device 206 is any type of device capable of being actuated by a user to generate a signal. Some non-limiting examples of HMI devices 206 include a push-button switch, a toggle switch, a capacitive switch, a rotary switch, a slide switch, and a rocker switch. In some embodiments, the loudspeaker 208 may be configured to present audio content, alerts, and other sounds. In some embodiments, the microphone 213 may be configured to receive audio input from the environment surrounding the personal care device 102. In some embodiments, further sensor components, such as one or more accelerometers, may be included in the personal care device 102. These senor components may be used to detect gestures, to detect drops and/or falls, or to detect other motions of the personal care device 102 that can then be used to control the treatment application device 202 or to transmit signals to the networked computing device 104 based on the detected gestures, falls, or other motions.

In some embodiments, the processor 210 is configured to execute computer-executable instructions stored on the computer-readable medium 214. The processor 210 may also be configured to receive and transmit signals to and/or from the other components of the personal care device 102 via a communication bus or other circuitry. In some embodiments, the network interface 212 is configured to transmit and receive signals to and from the networked computing device 104 on behalf of the processor 210. The network interface 212 may implement any suitable networking technology, including but not limited to short-range wireless technologies such as Bluetooth, infrared, near-field communication, and Wi-Fi; long-range wireless technologies such as WiMAX, 2G, 3G, 4G, and LTE; and wired technologies such as USB, FireWire, and Ethernet. In some embodiments, the computer-readable medium 214 is any type of computer-readable medium on which computer-executable instructions may be stored, including but not limited to a flash memory, a ROM, an EPROM, an EEPROM, and an FPGA. In some embodiments, the computer-readable medium 214 and the processor 210 may be combined into a single device, such as an ASIC, or the computer-readable medium 214 may include a cache memory, a register, or another component of the processor 210.

In the illustrated embodiment, the computer-readable medium 214 has computer-executable instructions stored thereon that, in response to execution by the processor 210, cause the personal care device 102 to provide an alert handling engine 216 and a treatment control engine 218. In general, the word "engine," as used herein, refers to logic embodied in hardware or software instructions, which can be written in a programming language, such as C, C++, COBOL, JAVA™, PHP, Perl, HTML, CSS, JavaScript, VBScript, ASPX, Microsoft.NET™, and/or the like. An engine may be compiled into executable programs or written in interpreted programming languages. Software engines may be callable from other engines or from themselves. Generally, the engines described herein refer to logical modules that can be merged with other engines, or can be divided into sub engines. The engines can be stored in any type of computer readable medium or computer storage device and be stored on and executed by one or more general purpose computers, thus creating a special purpose computer configured to provide the engine or the functionality thereof.

In some embodiments, the treatment control engine 218 detects actuation of the HMI device 206, and activates the treatment application device 202 in response. In some embodiments, the treatment control engine 218 may allow the treatment application device 202 to operate for a predetermined amount of time before automatically deactivating the treatment application device 202. In some embodiments, the treatment control engine 218 may also detect actuations of the HMI device 206 while the treatment application device 202 is already activated, and may take action in response based on a mode in which the personal care device 102 is operating. In some embodiments, the alert handling engine 216 switches the mode in which the personal care device 102 is operating based on signals received by the network interface 212.

Further details of the functionality of the components of the personal care device 102 are provided below.

Figure 3:
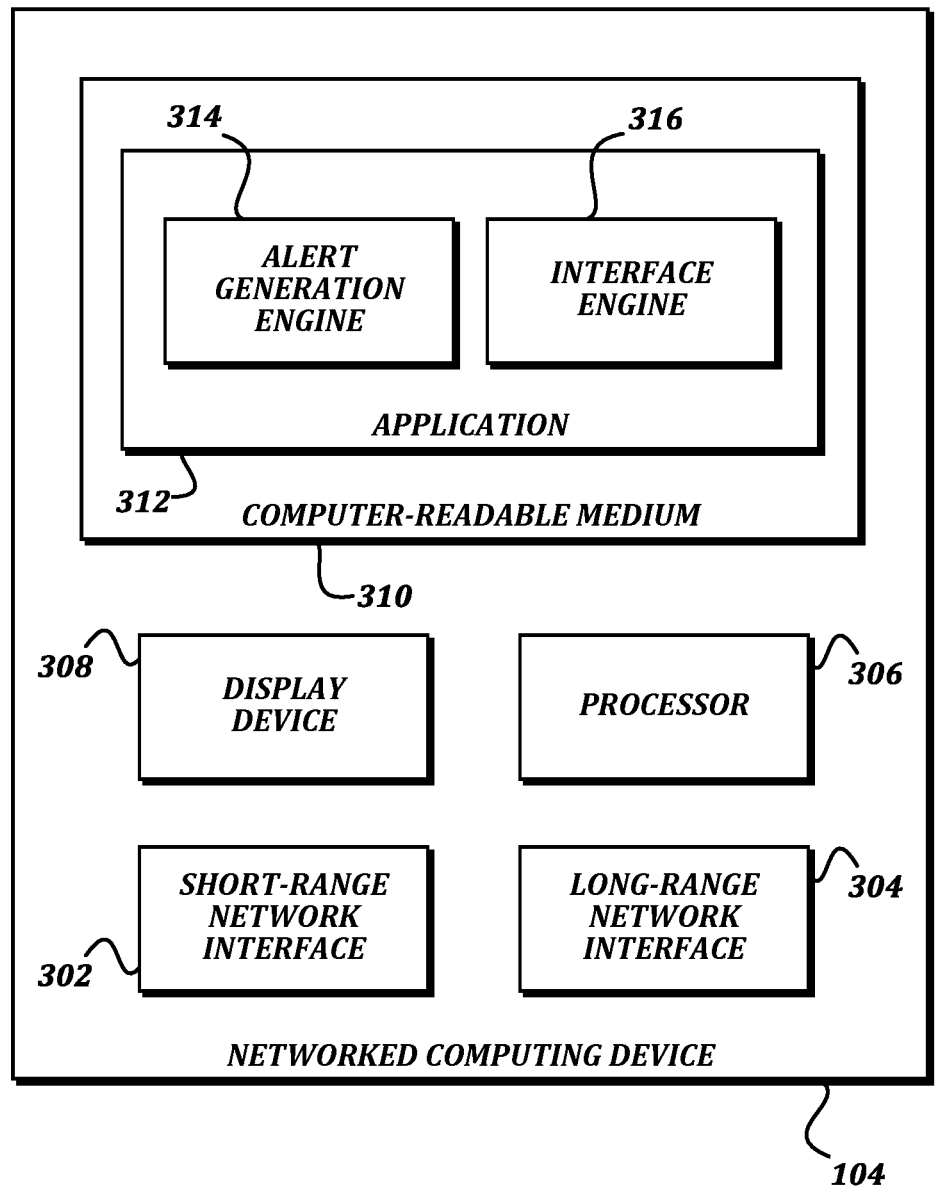
FIG. 3 is a block diagram that illustrates components included in an example embodiment of a networked computing device according to various aspects of the present disclosure.

FIG. 3 is a block diagram that illustrates components included in an example embodiment of a networked computing device according to various aspects of the present disclosure. The networked computing device 104 may be a computing device of any form factor that is capable of communicating with the personal care device 102, and of performing the other actions described herein as being performed by the networked computing device 104. In some embodiments, the networked computing device 104 may be a mobile computing device such as a smartphone or a tablet computing device. In some embodiments, the networked computing device 104 may be a desktop computing device or a laptop computing device.

In the illustrated embodiment, the networked computing device 104 includes a short-range network interface 302, a long-range network interface 304, a processor 306, a display device 308, and a computer-readable medium 310.

In some embodiments, the short-range network interface 302 is configured to transmit and receive signals to and from the personal care device 102 on behalf of the processor 306. The short-range network interface 302 may implement any suitable networking technology, and implements a complementary technology to that implemented by the network interface 212 of the personal care device 102. In some embodiments, the long-range network interface 304 is configured to transmit and receive signals to and from one or more remote systems, including but not limited to e-mail systems, mobile telephony systems, social networking systems, and short messaging service (SMS) systems. The long-range network interface 304 may implement any suitable networking technology capable of communicatively coupling the networked computing device 104 to the remote systems, including but not limited to wired technologies such as Ethernet, USB, and FireWire; and wireless technologies such as Wi-Fi, WiMAX, 2G, 3G, 4G, LTE, Bluetooth, infrared, and NFC. The short-range network interface 302 and the long-range network interface 304 are described as "short range" and "long range" for convenience only, and these descriptors should not be seen as limiting with respect to the relative distances between the personal care device 102, the networked computing device 104, and any remote systems.

In some embodiments, the display device 308 is configured to present one or more graphical user interfaces, including but not limited to a graphical user interface generated by the application 312. In some embodiments, the display device 308 may also be configured to receive inputs from a user, such as a touchscreen device.

In some embodiments, the processor 306 is configured to execute computer-executable instructions stored on the computer-readable medium 310. The processor 306 may also be configured to receive and transmit signals to and/or from the other components of the networked computing device 104 via a communication bus or other circuitry.

In some embodiments, the computer-readable medium 310 has computer-executable instructions stored thereon that, in response to execution by the processor 306, cause the networked computing device 104 to provide an application 312. The computer-readable medium 310 may be any suitable type of computer-readable medium 310, including but not limited to flash memory, a hard disk drive, or any other type of non-transitory computer-readable medium.

In some embodiments, the application 312 may be installed on the networked computing device 104 after being downloaded from an app store or other distribution point. In some embodiments, the application 312 may be a web-based application, and components may be downloaded and executed within a web browser or other thin interface installed on the networked computing device 104.

In the illustrated embodiment, the application 312 includes an alert generation engine 314 and an interface engine 316. In some embodiments, the alert generation engine 314 determines when alerts should be generated (for example, in response to an incoming message received via the long-range network interface 304 such as an email, a text message, or a push notification; in response to time-based alarms generated by the networked computing device 104, or in response to any other appropriate condition), and transmits the alerts to the personal care device 102 for processing. In some embodiments, the interface engine 316 generates a graphical user interface to be presented via the display device 308. The graphical user interface may be used to configure alerts to be transmitted to the personal care device 102, to provide commands to the personal care device 102 regarding how to handle various alerts, or to provide other functionality related to the system.

Further details of the functionality of the components of the networked computing device 104 are provided below.

Figure 4A:
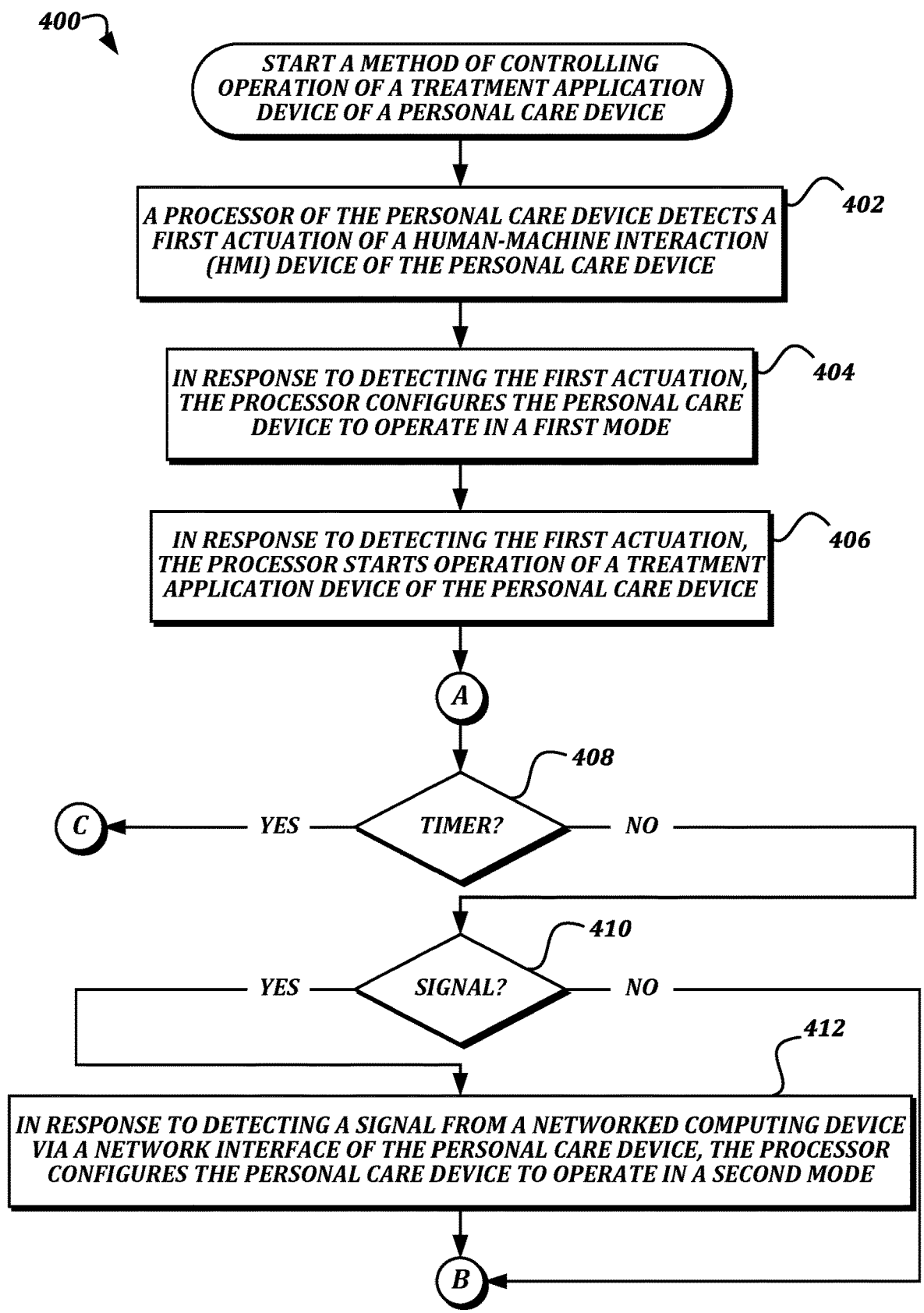
FIGS. 4A-4B are a flowchart that illustrates an example embodiment of a method of controlling operation of a treatment application device of a personal care device according to various aspects of the present disclosure.
Figure 4B:
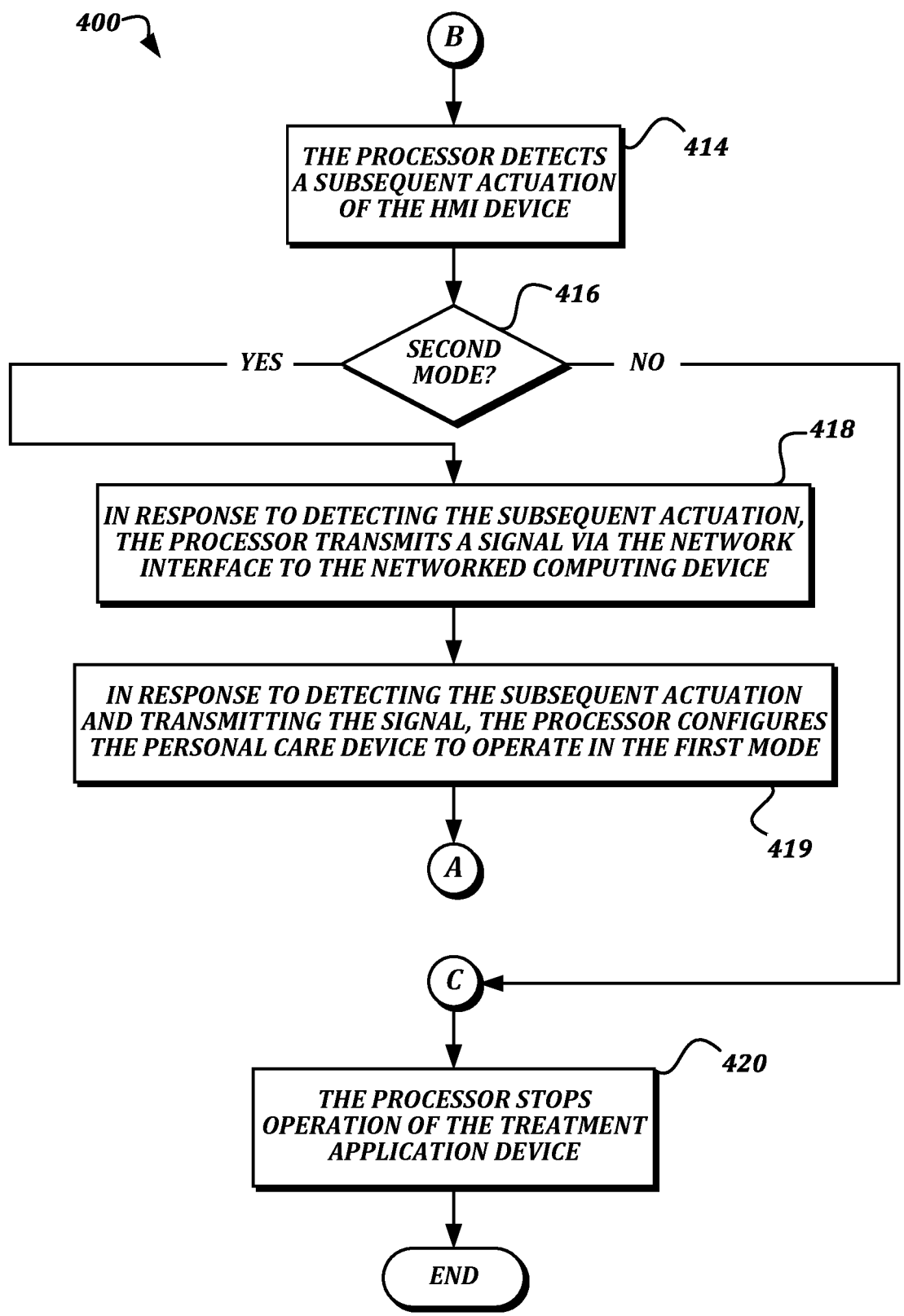

FIGS. 4A-4B are a flowchart that illustrates an example embodiment of a method of controlling operation of a treatment application device of a personal care device according to various aspects of the present disclosure. By using an embodiment of the method 400 illustrated in FIGS. 4A-4B, a single HMI device 206 of the personal care device 102 can be used to both control starting/stopping of the treatment application device 202, as well as for sending a signal to the networked computing device 104 in order to cancel or otherwise address an alert or alarm generated by the networked computing device 104 while the treatment application device 202 is operating.

From a start block, the method 400 proceeds to block 402, where a processor 210 of the personal care device 102 detects a first actuation of a human-machine interaction (HMI) device 206 of the personal care device 102. For example, if the HMI device 206 is a push-button switch, the processor 210 may receive a signal that indicates that the push-button switch was pressed.

At block 404, in response to detecting the first actuation, the processor 210 configures the personal care device 102 to operate in a first mode. In some embodiments, the first mode may include allowing the treatment application device 202 to operate until either a predetermined amount of time elapses or a subsequent actuation of the HMI device 206 is detected. In some embodiments, configuring the personal care device 102 to operate in the first mode may include setting a flag or other value in a computer-readable medium that is accessible by the processor 210 and/or the treatment control engine 218. In some embodiments, the flag may be consulted by the treatment control engine 218 and/or by other instructions executed by the processor 210 in response to a subsequent detection of an actuation of the HMI device 206, as discussed below.

At block 406, in response to detecting the first actuation, the processor 210 starts operation of a treatment application device 202 of the personal care device 102. In some embodiments, starting operation of the treatment application device 202 may include providing power from the power storage source 204 to cause the treatment application device 202 to operate. For example, if the treatment application device 202 includes a drive motor, starting operation of the treatment application device 202 may include causing the drive motor to run. As another example, if the treatment application device 202 includes a light-emitting component, starting operation of the treatment application device 202 may include causing the light-emitting component to begin emitting light.

The method 400 then proceeds to a continuation terminal ("terminal A"), and from terminal A to a decision block 408, where a determination is made regarding whether a timer for the operation of the treatment application device 202 has expired. In some embodiments, the timer is an elapsed time measured by the processor 210, and measures an amount of time since the start of operation of the treatment application device 202. For example, the timer may be used to measure 60 seconds from the start of the operation of the treatment application device 202, such that the treatment is applied for 60 seconds. If the timer has expired, then the result of decision block 408 is YES, and the method 400 proceeds to another continuation terminal ("terminal C") to continue with a process of stopping operation of the treatment device (due to the expiration of the timer).

Otherwise, if the timer has not expired, then the result of decision block 408 is NO, and the method 400 proceeds to another decision block 410, where a determination is made regarding whether a signal has been received from a networked computing device 104 while the treatment application device 202 continues to operate. The signal may be received by the processor 210 via the network interface 212 from the networked computing device 104. The signal indicates an alert that was generated by the alert generation engine 314 of the networked computing device 104 in response to receiving a network message, generation of an alarm, or any other event at the networked computing device 104 that would cause the networked computing device 104 to generate an alert.

If a signal has not been received, then the result of decision block 410 is NO, and the method 400 proceeds to another continuation terminal ("terminal B"). Otherwise, if a signal has been received, then the result of decision block 410 is YES, and the method 400 proceeds to block 412.

At block 412, in response to detecting a signal from a networked computing device 104 via a network interface 212 of the personal care device 102, the processor 210 configures the personal care device 102 to operate in a second mode. In some embodiments, the second mode changes what happens in response to detecting an actuation of the HMI device 206, though a timer may still control the treatment application device 202 in the absence of detecting an actuation of the HMI device 206. In some embodiments, configuring the personal care device 102 to operate in the second mode includes changing a value of the flag or other value set at block 404. The method 400 then proceeds to terminal B. In some embodiments, the personal care device 102 may also use the loudspeaker 208 or a change in the operation of the treatment application device 202 (such as a pause, or a change in a vibration pattern) to notify a user that the signal has been received.

From terminal B (FIG. 4B), the method 400 proceeds to block 414, where the processor 210 detects a subsequent actuation of the HMI device 206. The method 400 then proceeds to a decision block 416, where a determination is made regarding whether the personal care device 102 is operating in the first mode (having not received a signal from the networked computing device 104) or the second mode (having received a signal from the networked computing device 104). In some embodiments, the determination may be based on whether the flag or other value discussed above has been set to indicate operation in the second mode. If the personal care device 102 is operating in the second mode, then the result of decision block 416 is YES, and the method 400 proceeds to block 418, where, in response to detecting the subsequent actuation, the processor 210 transmits a signal via the network interface 212 to the networked computing device 104. In some embodiments, the signal may be used by the networked computing device 104 to cancel an alarm being presented by the networked computing device 104, send an automatic response to a message received by the networked computing device 104, or perform any other suitable action in response to the alert. At block 419, in response to detecting the subsequent actuation and transmitting the signal, the processor 210 configures the personal care device 102 to operate in the first mode. In some embodiments, the processor 210 may configure the personal care device 102 to operate in the first mode by resetting the flag or other value discussed above. The method 400 then returns to terminal A in order to continue operating the treatment application device 202 until the timer elapses, another actuation of the HMI device 206 is detected, or another alert is received.

Returning to decision block 416, if the personal care device 102 is not operating in the second mode 416, then the result of decision block 416 is NO, and the method 400 proceeds to terminal C. The method 400 arrives at terminal C either in response to the timer elapsing or in response to detecting an actuation of the HMI device 206 while operating in the first mode. From terminal C, the method 400 proceeds to block 420, where the processor 210 stops operation of the treatment application device 202. The method 400 then proceeds to an end block and terminates.

Figure 5:
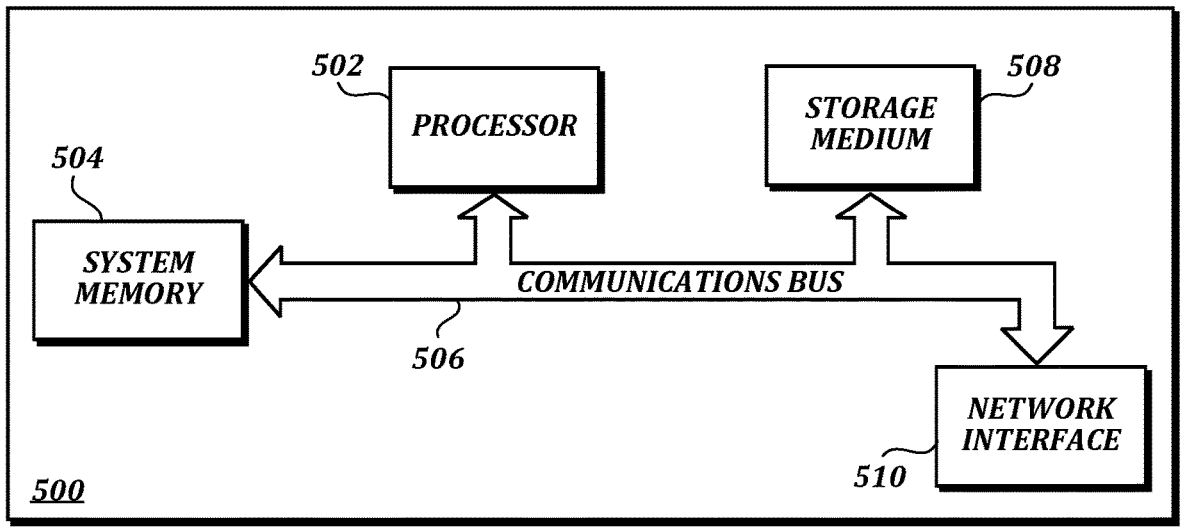
FIG. 5 is a block diagram that illustrates aspects of an exemplary computing device appropriate for use with embodiments of the present disclosure.

FIG. 5 is a block diagram that illustrates aspects of an exemplary computing device appropriate for use with embodiments of the present disclosure. While FIG. 5 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 500 may be any one of any number of currently available or yet to be developed devices.

In its most basic configuration, the computing device 500 includes at least one processor 502 and a system memory 504 connected by a communication bus 506. Depending on the exact configuration and type of device, the system memory 504 may be volatile or nonvolatile memory, such as read only memory ("ROM"), random access memory ("RAM"), EEPROM, flash memory, or similar memory technology. Those of ordinary skill in the art and others will recognize that system memory 504 typically stores data and/or program modules that are immediately accessible to and/or currently being operated on by the processor 502. In this regard, the processor 502 may serve as a computational center of the computing device 500 by supporting the execution of instructions.

As further illustrated in FIG. 5, the computing device 500 may include a network interface 510 comprising one or more components for communicating with other devices over a network. Embodiments of the present disclosure may access basic services that utilize the network interface 510 to perform communications using common network protocols. The network interface 510 may also include a wireless network interface configured to communicate via one or more wireless communication protocols, such as WiFi, 2G, 3G, 4G, LTE, WiMAX, Bluetooth, and/or the like.

In the exemplary embodiment depicted in FIG. 5, the computing device 500 also includes a storage medium 508. However, services may be accessed using a computing device that does not include means for persisting data to a local storage medium. Therefore, the storage medium 508 depicted in FIG. 5 is represented with a dashed line to indicate that the storage medium 508 is optional. In any event, the storage medium 508 may be volatile or nonvolatile, removable or nonremovable, implemented using any technology capable of storing information such as, but not limited to, a hard drive, solid state drive, CD-ROM, DVD, or other disk storage, magnetic cassettes, magnetic tape, magnetic disk storage, and/or the like.

As used herein, the term "computer-readable medium" includes volatile and nonvolatile and removable and non-removable media implemented in any method or technology capable of storing information, such as computer-readable instructions, data structures, program modules, or other data. In this regard, the system memory 504 and storage medium 508 depicted in FIG. 5 are merely examples of computer-readable media.

Suitable implementations of computing devices that include a processor 502, system memory 504, communication bus 506, storage medium 508, and network interface 510 are known and commercially available. For ease of illustration and because it is not important for an understanding of the claimed subject matter, FIG. 5 does not show some of the typical components of many computing devices. In this regard, the computing device 500 may include input devices, such as a keyboard, keypad, mouse, microphone, touch input device, touch screen, tablet, and/or the like. Such input devices may be coupled to the computing device 500 by wired or wireless connections including RF, infrared, serial, parallel, Bluetooth, USB, or other suitable connections protocols using wireless or physical connections. Similarly, the computing device 500 may also include output devices such as a display, speakers, printer, etc. Since these devices are well known in the art, they are not illustrated or described further herein. Unless specifically defined herein, all terms used herein have the same meaning as they would to one skilled in the art of the present disclosure.

While illustrative embodiments have been illustrated and described, it will be appreciated that various changes can be made therein without departing from the spirit and scope of the invention.

The invention claimed is:

1. A method of controlling operation of a treatment application device of a personal care device, the method comprising:
   starting the treatment application device in response to detecting a first actuation of a human-machine interface (HMI) device of the personal care device; and
   while the treatment application device is running and in response to detecting a second actuation of the HMI device:
      determining whether the personal care device is operating in a first mode that indicates that the personal care device has not received an incoming signal from a networked computing device via a network interface of the personal care device or a second mode that indicates that the personal care device has received the incoming signal from the networked computing device via the network interface of the personal care device;
      stopping the treatment application device in response to determining that the personal care device is operating in the first mode that indicates that the personal care device has not received the incoming signal from the networked computing device; and
      transmitting, via the network interface, an outgoing signal to the networked computing device without stopping the treatment application device in response to determining that the personal care device is operating in the second mode that indicates that the personal care device has received the incoming signal from the networked computing device.

2. The method of claim 1, wherein the incoming signal indicates an event detected by the networked computing device.

3. The method of claim 1, further comprising presenting a notification in response to receiving the incoming signal from the networked computing device.

4. The method of claim 3, wherein presenting the notification includes at last one of:
   altering a vibration pattern of the treatment application device;
   altering a flashing pattern of a light emitting component of the treatment application device; and
   emitting a tone from a loudspeaker of the treatment application device.

5. The method of claim 1, wherein the outgoing signal causes the networked computing device to cancel an alarm generated by the networked computing device.

6. The method of claim 1, wherein the HMI device includes a push button switch.

7. A personal care device, comprising:
   a treatment application device;
   a human-machine interface (HMI) device;
   a network interface; and
   a non-transitory computer-readable medium having computer-executable instructions stored thereon that, in response to execution by the personal care device, cause the personal care device to perform actions comprising:
      detecting a first actuation of the HMI device;
      starting the treatment application device in response to detecting the first actuation of the HMI device; and
      while the treatment application device is running:
         receiving an incoming signal from a networked computing device via the network interface;
         detecting a second actuation of the HMI device after receiving the incoming signal;
         transmitting, via the network interface, an outgoing signal to the networked computing device without stopping the treatment application device in response to detecting the second actuation of the HMI device after receiving the incoming signal;
         detecting a third actuation of the HMI device after transmitting the outgoing signal; and
         stopping the treatment application device in response to detecting the third actuation of the HMI device after transmitting the outgoing signal.

8. The personal care device of claim 7, wherein the incoming signal indicates an event detected by the networked computing device.

9. The personal care device of claim 7, wherein the actions further comprise presenting a notification in response to receiving the incoming signal from the networked computing device.

10. The personal care device of claim 9, wherein presenting the notification includes at last one of:
- altering a vibration pattern of the treatment application device;
- altering a flashing pattern of a light emitting component of the treatment application device; and
- emitting a tone from a loudspeaker of the treatment application device.

11. The personal care device of claim 7, wherein the outgoing signal causes the networked computing device to cancel an alarm generated by the networked computing device.

12. The personal care device of claim 7, wherein the HMI device includes a push button switch.

13. A system, comprising:
- circuitry for starting a treatment application device of a personal care device in response to detecting a first actuation of a human-machine interface (HMI) device of the personal care device; and
- circuitry for, while the treatment application device is running and in response to detecting a second actuation of the HMI device:
  - determining whether the personal care device is operating in a first mode that indicates that the personal care device has not received an incoming signal from a networked computing device via a network interface of the personal care device or a second mode that indicates that the personal care device has received the incoming signal from the networked computing device via the network interface of the personal care device;
  - stopping the treatment application device in response to determining that the personal care device is operating in the first mode that indicates that the personal care device has not received the incoming signal from the networked computing device; and
  - transmitting, via the network interface, an outgoing signal to the networked computing device without stopping the treatment application device in response to determining that the personal care device is operating in the second mode that indicates that the personal care device has received the incoming signal from the networked computing device.

14. The system of claim 13, wherein the incoming signal indicates an event detected by the networked computing device.

15. The system of claim 13, further comprising circuitry for presenting a notification in response to receiving the incoming signal from the networked computing device.

16. The system of claim 15, wherein presenting the notification includes at last one of:
- altering a vibration pattern of the treatment application device;
- altering a flashing pattern of a light emitting component of the treatment application device; and
- emitting a tone from a loudspeaker of the treatment application device.

17. The system of claim 13, wherein the outgoing signal causes the networked computing device to cancel an alarm generated by the networked computing device.

* * * * *